US010607397B2

(12) United States Patent
Short et al.

(10) Patent No.: US 10,607,397 B2
(45) Date of Patent: Mar. 31, 2020

(54) GENERATING THREE DIMENSIONAL MODELS

(71) Applicant: Hewlett-Packard Development Company, L.P., Houston, TX (US)

(72) Inventors: David Bradley Short, San Diego, CA (US); Stephen George Miller, Salt Lake City, UT (US); Jordi Morillo Peres, Barcelona (ES); Jinman Kang, San Diego, CA (US); Patricia Panqueva, Palo Alto, CA (US); Matthew Leck, San Francisco, CA (US); Daniel Jordan Kayser, San Francisco, CA (US); Eddie Licitra, San Francisco, CA (US)

(73) Assignee: Hewlett-Packard Development Company, L.P., Spring, TX (US)

( * ) Notice: Subject to any disclaimer, the term of this patent is extended or adjusted under 35 U.S.C. 154(b) by 66 days.

(21) Appl. No.: 15/557,604

(22) PCT Filed: Jun. 4, 2015

(86) PCT No.: PCT/US2015/034269
§ 371 (c)(1),
(2) Date: Sep. 12, 2017

(87) PCT Pub. No.: WO2016/195694
PCT Pub. Date: Dec. 8, 2016

(65) Prior Publication Data
US 2018/0061120 A1 Mar. 1, 2018

(51) Int. Cl.
*G06T 19/20* (2011.01)
*G06T 15/20* (2011.01)
(Continued)

(52) U.S. Cl.
CPC .......... *G06T 15/205* (2013.01); *A61B 5/0033* (2013.01); *A61B 5/0064* (2013.01);
(Continued)

(58) Field of Classification Search
CPC ................ G06T 17/20; G06T 19/00
(Continued)

(56) References Cited

U.S. PATENT DOCUMENTS 6,925,198 B2 8/2005 Scharlack et al.
7,474,803 B2 1/2009 Petrov et al.
(Continued)

FOREIGN PATENT DOCUMENTS

CN      1669069 A      9/2005
CN    101320473 A     12/2008
WO  WO-2009/120073 A2  10/2009

OTHER PUBLICATIONS

Kelly Tse et al., "Use of Laser 3D Surface Digitizer in Data Collection and 3d Modeling of Anatomical Structures," Feb. 2006, pp. 1-2.

*Primary Examiner* — Jin Ge
(74) *Attorney, Agent, or Firm* — HP Inc. Patent Department

(57) ABSTRACT

Examples relate to capturing and processing three dimensional (3D) scan data. In some examples, 3D scan data of a real-world object is obtained while the real-world object is repositioned in a number of orientations, where the 3D scan data includes 3D scan passes that are each associated with one of the orientations. A projector is used to project a visual cue related to a position of the real-world object as the real-world object is repositioned at each of the orientations. The 3D scan passes are stitched to generate a 3D model of the real-world object, where a real-time representation of the 3D model is shown on a display as each of the 3D scan passes is incorporated into the 3D model.

12 Claims, 5 Drawing Sheets

(51) Int. Cl.
*A61B 5/00* (2006.01)
*G01B 11/24* (2006.01)
*G06T 17/00* (2006.01)
*G06T 17/20* (2006.01)

(52) U.S. Cl.
CPC .............. *G01B 11/24* (2013.01); *G06T 17/00* (2013.01); *G06T 17/205* (2013.01); *G06T 19/20* (2013.01); *A61B 5/0073* (2013.01); *A61B 5/7203* (2013.01)

(58) Field of Classification Search
USPC ........................................................ 345/420
See application file for complete search history.

(56) References Cited

U.S. PATENT DOCUMENTS

| | | | | |
|---|---|---|---|---|
| 8,773,514 | B2 | 7/2014 | Gharib et al. | |
| 8,848,201 | B1* | 9/2014 | Bruce | G01B 21/047 |
| | | | | 356/601 |
| 2004/0223077 | A1* | 11/2004 | Said | H04N 13/021 |
| | | | | 348/370 |
| 2006/0188143 | A1 | 8/2006 | Strassenburg-Kleciak | |
| 2008/0101688 | A1 | 5/2008 | Quadling et al. | |
| 2008/0181496 | A1* | 7/2008 | Ferman | G06K 9/00456 |
| | | | | 382/168 |
| 2009/0167843 | A1* | 7/2009 | Izzat | G06T 7/593 |
| | | | | 348/43 |
| 2010/0179420 | A1* | 7/2010 | Ernst | A61B 5/0073 |
| | | | | 600/425 |
| 2012/0062557 | A1* | 3/2012 | Dillon | A61C 7/002 |
| | | | | 345/419 |
| 2013/0206985 | A1 | 8/2013 | Turner et al. | |
| 2013/0335417 | A1* | 12/2013 | McQueston | A61B 6/145 |
| | | | | 345/424 |
| 2014/0063204 | A1 | 3/2014 | Siercks | |
| 2014/0125768 | A1 | 5/2014 | Bell et al. | |
| 2014/0218480 | A1* | 8/2014 | Knighton | G01B 11/24 |
| | | | | 348/46 |
| 2015/0009214 | A1 | 1/2015 | Lee et al. | |
| 2015/0015701 | A1 | 1/2015 | Yu | |
| 2015/0043788 | A1* | 2/2015 | Lee | G06K 9/00362 |
| | | | | 382/110 |
| 2016/0259515 | A1* | 9/2016 | Sabina | A61C 9/0053 |
| 2016/0324664 | A1* | 11/2016 | Piron | A61F 2/46 |

* cited by examiner

GENERATING THREE DIMENSIONAL MODELS

BACKGROUND

A three-dimensional (3D) model of an object has many uses. A 3D model can be used in a variety of applications including, but not limited to, movie and video game assets, medical orthotics and prosthetics, industrial design, etc.

BRIEF DESCRIPTION OF THE DRAWINGS

The following detailed description references the drawings, wherein.

DETAILED DESCRIPTION

A capture system may be used to digitally capture data related to the shape and appearance of a real-world object. The captured data can then be used to construct a three-dimensional (3D) model of the object. Different techniques can be used to collect data related to the shape of a real-world object such as contact scanners, time-of-flight laser scanners, triangulation laser scanners, structured light scanners, etc. For example, a hand-held device can be used to collect shape data by making distance measurements while the hand-held device is repositioned. In this example, the hand-held device tracks its position using an internal coordinate system, which is used to reference the distance measurements.

Examples herein describe 3D capture techniques that allow the user to place an object surface and scan it to create a complete 3D model from all sides. The model produced is a 3D mesh with texture, and the scan process involves progressively scanning the object from varying orientations and stitching these scans together to create a single, complete model. Each incremental scan is aligned to fit to and extend the existing model.

In some examples, 3D scan data of a real-world object is obtained while the real-world object is repositioned in a number of orientations, where the 3D scan data includes 3D scan passes that are each associated with one of the orientations. A projector is used to project a visual cue related to a position of the real-world object as the real-world object is repositioned at each of the orientations. The 3D scan passes are stitched to generate a 3D model of the real-world object, where a real-time representation of the 3D model is shown on a display as each of the 3D scan passes is incorporated into the 3D model.

Figure 1:
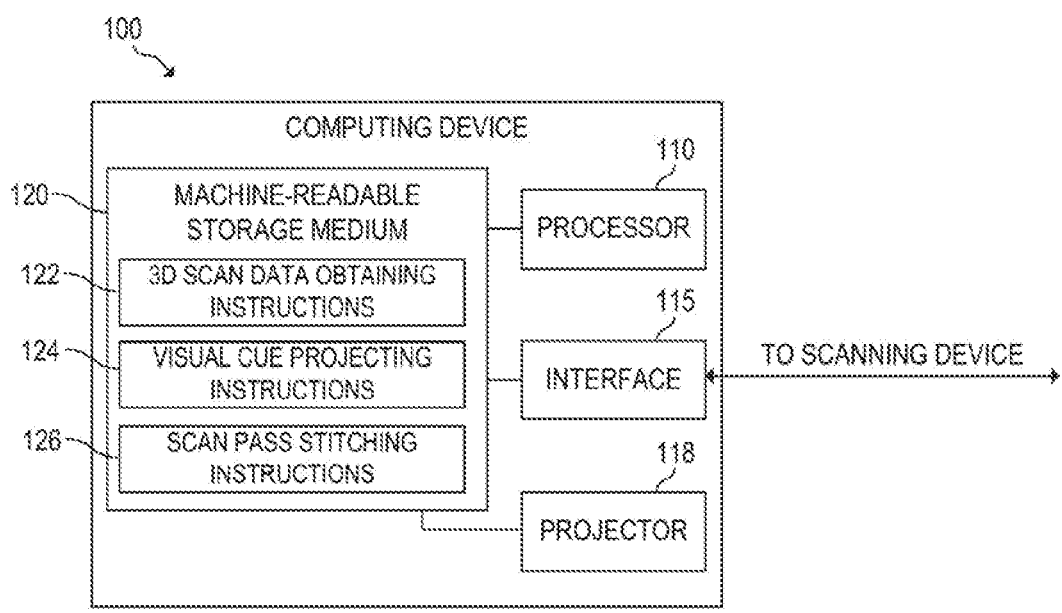
FIG. 1 is a block diagram of an example computing device for capturing and processing 3D scan data.

Referring now to the drawings, FIG. 1 is a block diagram of an example computing device 100 for capturing and processing 3D scan data. Computing device 100 may be any computing device (e.g., smartphone, tablet, laptop computer, desktop computer, etc.) with access to a scanning device. In the embodiment of FIG. 1, computing device 100 includes a processor 110, an interface 115, a projector 118, and a machine-readable storage medium 120.

Processor 110 may be one or more central processing units (CPUs), microprocessors, and/or other hardware devices suitable for retrieval and execution of instructions stored in machine-readable storage medium 120. Processor 110 may fetch, decode, and execute instructions 122, 124, 126 to enable detection of a receiving user for capturing and processing 3D scan data. As an alternative or in addition to retrieving and executing instructions, processor 110 may include one or more electronic circuits comprising a number of electronic components for performing the functionality of one or more of instructions 122, 124, 126.

Interface 115 may include a number of electronic components for communicating with a scanning device. For example, interface 115 may be an Ethernet interface, a Universal Serial Bus (USB) interface, an IEEE 1394 (Firewire) interface, an external Serial Advanced Technology Attachment (eSATA) interface, or any other physical connection interface suitable for communication with the scanning device. Alternatively, interface 115 may be a wireless interface, such as a wireless local area network (WLAN) interface or a near-field communication (NFC) interface. In operation, as detailed below, interface 115 may be used to send and receive data to and from a corresponding interface of the scanning device.

Projector 118 is an optical device for projecting images onto a surface. For example, projector 118 may be an embedded light source, a laser, video projector, or any other optical device suitable for projecting images.

Machine-readable storage medium 120 may be any electronic, magnetic, optical, or other physical storage device that stores executable instructions. Thus, machine-readable storage medium 120 may be, for example, Random Access Memory (RAM), an Electrically-Erasable Programmable Read-Only Memory (EEPROM), a storage drive, an optical disc, and the like. As described in detail below, machine-readable storage medium 120 may be encoded with executable instructions for capturing and processing 3D scan data.

3D scan data obtaining instructions 122 obtain 3D scan data from a scanning device. The scanning device is capable of capture shape and appearance data for a real-world object in the view of the scanning device. In some cases, the scanning device is a 3D camera equipped with multiple lenses that are capable of determining depth data for a real-world object in the view of the camera. The 3D scan data can be obtained via numerous scan passes, which each obtain shape and appearance information for the object at a different position and/or orientation. The scan passes can be part of a scan cycle that, for example, obtains scan data as the object is rotated a full cycle around a central axis. The rotation can be performed manually as described with respect to FIG. 4A or automatically as described with respect to FIG. 4B. In this example, the scanning device is connected to computing device 100 via interface 115. In other examples, the scanning device can be an integrated component of computing device 100.

Visual cue projecting instructions 124 uses projector 118 to project visual cues on the real-world object and the surface on which the object rests. The visual cues provide the user with information related to the position of the object. For example, the visual cues can include an indication of the direction that the object is facing. As a scan cycle is performed, the visual cues can also mark the scan passes that have already been completed for an object. When manual rotation is used for scanning, the visual cues can also direct the user on how to reposition the object for each of the 3D scan passes. Example visual cues as described below with respect to FIG. 5.

Scan pass stitching instructions 126 stitches the scan passes obtained above to create a 3D model. In some cases, the scan passes are stitched as each one is obtained by the scanning device (i.e., the 3D model is modified after each scan pass to include the latest 3D data). The 3D model can also be displayed for the user as it is modified for each scan pass. Stitching the scan passes combines the 3D data in each of the scan passes into a single 3D model. For example, distinctive features in the scan passes can be identified and used to align the data in the passes so that the data in the passes can be combined into a single model.

Figure 2:
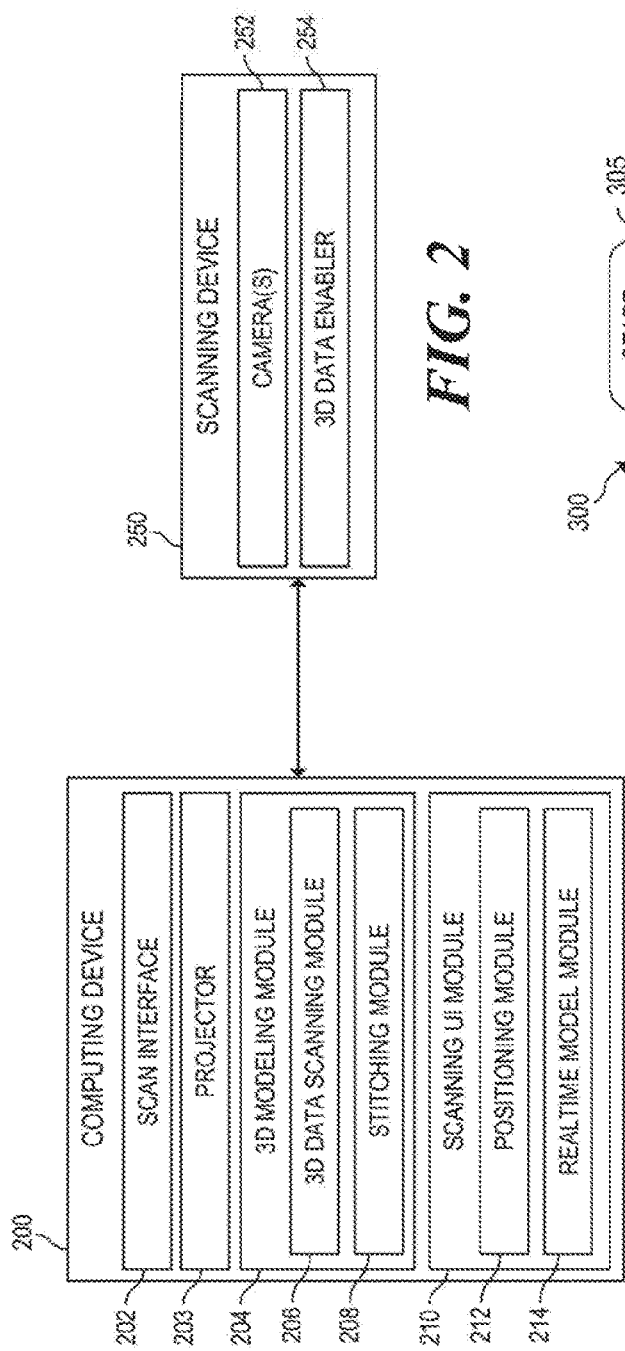
FIG. 2 is a block diagram of an example computing device in communication with a scanning device for capturing and processing 3D scan data.

FIG. 2 is a block diagram of an example scanning device 250 in communication via a network 245 with a computing device 200. As illustrated in FIG. 2 and described below, scanning device 250 may communicate with computing device 200 to capture and process 3D scan data.

As illustrated, computing device 200 may include a number of modules 202-214, while scanning device 250 may include a number of modules 252-254. Each of the modules may include a series of instructions encoded on a machine-readable storage medium and executable by a processor of the respective device 200, 250. In addition or as an alternative, each module may include one or more hardware devices including electronic circuitry for implementing the functionality described below.

As with computing device 100 of FIG. 1, computing device 200 may be a smartphone, notebook, desktop, tablet, workstation, mobile device, or any other device suitable for executing the functionality described below. As detailed below, computing device 200 may include a series of modules 202-214 for enabling capturing and processing 3D scan data.

Scan interface 202 may manage communications with the scanning device 250. Specifically, the scan interface 202 may initiate connections with the scanning device 250 and then send or receive scan data to/from the scanning device 250.

Projector 203 projects visual cues on and about a real-world object. For example, projector 203 can include light emitting diodes (LED's) for providing visual cues (i.e., scanned orientations, next orientation for scan cycle, etc.) during a scanning cycle. Scanning UI module 210 may use projector 203 during the scanning process to instruct a user on positioning the real-world object.

3D modeling module 204 may process scan data of scanning device 250 to generate 3D models. Although the components of 3D modeling module 204 are described in detail below, additional details regarding an example implementation of 3D modeling module 204 are provided above in connection with instructions 122 and 126 of FIG. 1.

3D data scanning module 206 obtains and processes scan data from scanning device 250. As the real-world object is repositioned, 3D data scanning module 206 can direct scanning device 250 to perform a scan cycle. A scan cycle includes a number of scan passes, each of which is taken while the object is in a different position and that can be combined to create a full 3D set of shape and appearance data for the object. For example, to scan the object in 3D, the scanning device 250 can project structured visible light and/or structured infrared light in a sequence of patterns on the object and capture and analyze the reflected light. The distortion of the structured light patterns on the object is then used to calculate the shape, depth and texture of the object. Scanning device 250 can also capture an image of the object to apply as surface texture for the model that is generated.

3D data scanning module 206 can also use scanning device 250 to perform a background scan. The background scan allows for the object to be distinguished the background (e.g., surface, rotating mechanism, etc.). A background scan can be performed before the object is placed on the surface. If a rotating mechanism is used, this background scan can also include multiple scans with the rotating mechanism automatically rotated to tilted and untilted positions.

3D data scanning module 206 can also use scanning device 250 to perform a prescan. During a prescan, scanning device 250 quickly scans the object while rotating it 360 degrees. The quick scan is used to obtain preliminary scan data for creating a preliminary object model, which allows the user to review the overall shape of the object and to observe how the scan process progressively adds detail.

Stitching module 208 creates 3D models based on the scan data obtained by 3D data scanning module 206. Specifically, stitching module 208 can stitch together scan passes of 3D scan data to create a full 3D model of a real-world object. Each scan pass can be stitched by stitching module 208 to previous scan pass as it is obtained by 3D data scanning module 206. For example, the scan passes can be analyzed to identify distinctive features of the object for overlaying the scan passes at the appropriate points. After all the scan passes are stitched, a full 3D model of the real-world object is created.

Scanning UI module 210 presents a user interface for performing a 3D scan of a real-world object (i.e., a user interface of a 3D scanning application). Although the components of scanning UI module 210 are described in detail below, additional details regarding an example implementation of scanning UI module 210 are provided above in connection with instructions 124 of FIG. 1.

Positioning module 212 can use projector 203 to provide visual cues as the object is repositioned for scanning. After 3D data scanning module 206 performs the prescan, positioning module 212 can provide the visual cues directly on the object and the surface surrounding it. The visual cues can be, for example, as described below with respect to FIG. 5. The visual cues can be updated by positioning module 212 as the scan passes are performed. For example, completed scan passes can be identified on the surface, and the position of the object for the next scan pass can also be shown.

For a manual scan, positioning module 212 guides the users to rotate the object on the surface manually. In the case a rotating mechanism is used, the object is rotated automatically, and the positioning module 212 can show the progress of the rotation and scan passes. At the end of the end of each 360 degree rotation (i.e., scan cycle), the user may inspect the model on a display of computing device 200, which can include rotating the model to examine the object from all sides. If the user chooses to continue scanning to improve the model, he may reposition the object to in a different orientation and continue with an additional scan cycle. The idea of rotating the object a full 360 degrees each time is to facilitate accuracy of stitching the individual scans.

Real-time model module 214 can show a real-time representation of the object (e.g., image stream from a camera) while a scan is being performed. As each scan pass is completed and the model is updated, the real-time representation can be updated to reflect new details from the scan pass. Real-time model can also allow the user to reposition the model in the user interface so that all sides of the model can be examined.

Scanning device 250 can be a peripheral or integrated component of computing device 200. Scanning device 250 is any device suitable of capturing 3D data such as a structured light camera device, a laser scanner, etc. As detailed below, scanning device 250 may include a series of modules 252-254 for capturing 3D data.

In FIG. 2, scanning device 250 includes camera(s) 252 for capturing structured light. For example, camera(s) 252 can include a combination of standard and infrared cameras, where a standard camera is used to capture texturing on the surface of the object and an infrared camera is used to capture shape data. The infrared camera can analyze a pattern of structured infrared light (e.g., star field, etc.) projected on the surface of the object to obtain the shape data. In this case, the structured infrared light can be projected by a 3D data enabler 254.

Figure 3:
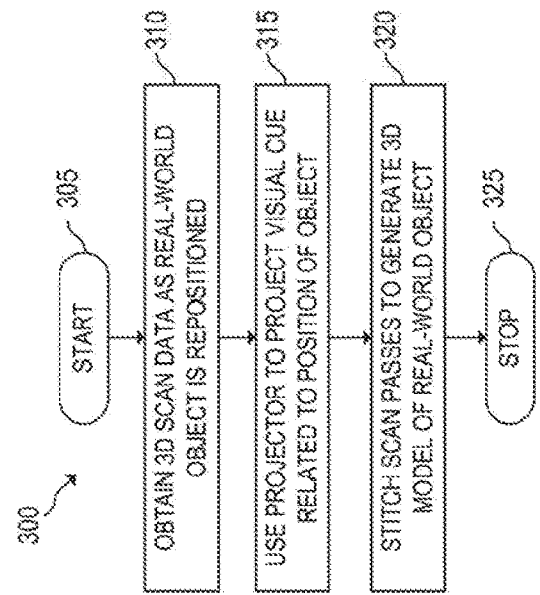
FIG. 3 is a flowchart of an example method for execution by a computing device for capturing and processing 3D scan data.

FIG. 3 is a flowchart of an example method 300 for execution by a computing device 100 for capturing and processing 3D scan data. Although execution of method 300 is described below with reference to computing device 100 of FIG. 1, other suitable devices for execution of method 300 may be used, such as computing device 200 of FIG. 2. Method 300 may be implemented in the form of executable instructions stored on a machine-readable storage medium, such as machine-readable storage medium 120, and/or in the form of electronic circuitry.

Method 300 may start in block 305 and continue to block 310, where computing device 100 obtains 3D scan data from a scanning device. The 3D scan data includes shape and appearance data for a real-world object in the view of the scanning device. In block 315, computing device 100 uses a projector to project visual cues on the real-world object and the surface on which the object rests. The visual cues can provide the user with information about a current scan cycle (e.g., position for next scan pass, completed scan passes, etc.) of the scanning device.

In block 320, computing device 100 stitches the scan passes obtained above to create a 3D model. In some cases, the scan passes are stitched as each one is obtained by the scanning device (i.e., the 3D model is modified after each scan pass to include the latest 3D data). Method 300 may subsequently proceed to block 325, where method 300 may stop.

Figure 4A:
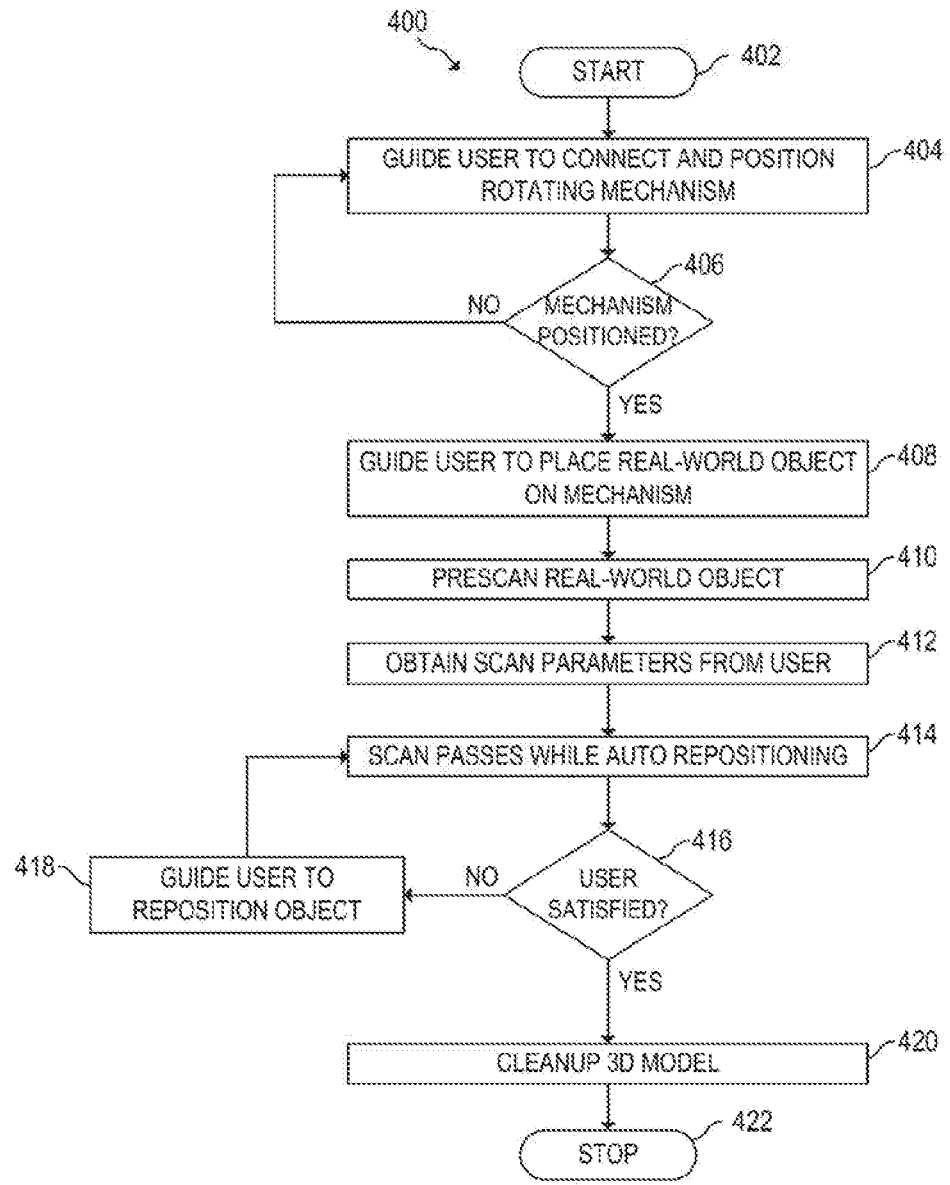
FIG. 4A is a flowchart of an example method for execution by a computing device for providing an automated 3D capture technique.

FIG. 4A is a flowchart of an example method 400 for execution by a computing device 100 for providing an automated 3D capture technique. Although execution of method 400 is described below with reference to computing device 100 of FIG. 1, other suitable devices for execution of method 400 may be used, such as computing device 200 of FIG. 2. Method 400 may be implemented in the form of executable instructions stored on a machine-readable storage medium, such as machine-readable storage medium 120, and/or in the form of electronic circuitry.

Method 400 may start in block 402 and continue to block 404, where computing device 100 guides a user to connect and position a rotating mechanism. For example, computing device 100 can project visual cues identifying a position and orientation for the rotating mechanism on a surface. In block 406, computing device 100 determines if the rotating mechanism is property positioned. If the rotating mechanism is not properly positioned, method 400 can return to block 404.

If the rotating mechanism is property positioned, computing device 100 guides the user to place a real-world object on the rotating mechanism in block 408. In block 410, computing device 100 performs a prescan of the object to generate a preliminary model. In block 412, computing device 100 obtains scan parameters from the user. For example, the user can specify a reference object that has a similar shape to the object being scanned.

In block 414, computing device 100 performs a scan cycle while automatically repositioning the object. Specifically, a rotating mechanism can rotate the object between scan passes so that scan data can be obtained for all sides of the object. As the scan passes are performed, the scan passes are stitched into the preliminary model to improve its detail. In block 416, computing device 100 determines if the user is satisfied with the 3D model.

If the user is not satisfied with the 3D model, computing device 100 guides the user to reposition the object for a second scan cycle in block 418. For example, computing device 100 can provide cycle instructions that instruct the user to change the tilt of the object on the rotating mechanism for the second scan cycle. After the object is repositioned on the rotating mechanism, method 400 returns to block 414 to perform the second scan cycle.

If the user is satisfied with the 3D model, computing device 100 cleans up the 3D model in block 420. For example, computing device 100 can remove artifacts from the 3D model. In this example, computing device 100 can also provide a user interface that allows the user to manually remove artifacts. To clean up the 3D model, computing device 100 can also finalize the stitching of the 3D model (i.e., stitch all of the scanning passes). Method 400 may subsequently proceed to block 422, where method 400 may stop.

Figure 4B:
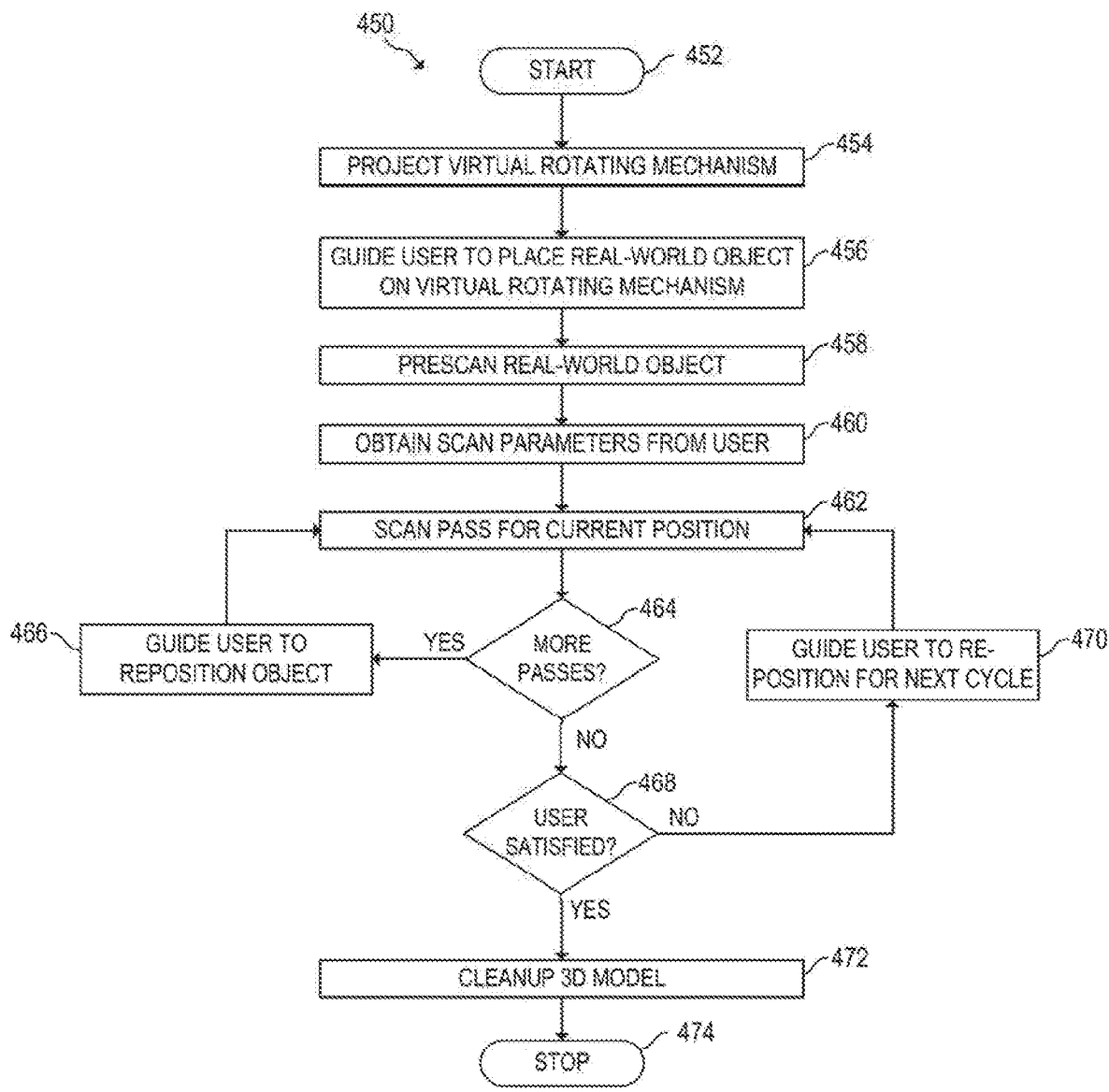
FIG. 4B is a flowchart of an example method for execution by a computing device for providing a manual 3D capture technique.

FIG. 4B is a flowchart of an example method 450 for execution by a computing device 100 for providing a manual 3D capture technique. Although execution of method 450 is described below with reference to computing device 100 of FIG. 1, other suitable devices for execution of method 450 may be used, such as computing device 200 of FIG. 2. Method 450 may be implemented in the form of executable instructions stored on a machine-readable storage medium, such as machine-readable storage medium 120, and/or in the form of electronic circuitry.

Method 450 may start in block 452 and continue to block 454, where computing device 100 projects a virtual rotating mechanism on a surface. For example, the virtual rotating mechanism can be as described below with respect to FIG. 5. In block 456, computing device 100 guides a user to place a real-world object on the virtual rotating mechanism. For example, computing device 100 can project visual cues identifying a position and orientation for the object on the surface.

In block 458, computing device 100 performs a prescan of the object to generate a preliminary model. In block 460, computing device 100 obtains scan parameters from the user. For example, the user can specify a reference object that has a similar shape to the object being scanned.

In block 462, computing device 100 performs a scan pass for the current position of the object. As the scan pass is performed, the scan pass is stitched into the preliminary model to improve its detail. In block 464, computing device 100 determines if there are more scan passes to perform (i.e., whether the scan cycle is complete). If there are more scan passes to perform, computing device 100 guides the user to rotate the object on the virtual rotating mechanism in block 466. Specifically, computing device 100 may provide a target visual cue that directs the user to reposition the object to a target position. After the object is manually rotated, method 400 returns to block 462, where computing device 100 performs the next scan pass.

If there are no more scan passes to perform, computing device 100 determines if the user is satisfied with the 3D model in block 468. If the user is not satisfied with the 3D model, computing device 100 guides the user to reposition the object for a second scan cycle in block 470. For example, computing device 100 can provide cycle instructions that instruct the user to change the tilt of the object on the virtual rotating mechanism for the second scan cycle. After the object is repositioned on the virtual rotating mechanism, method 450 returns to block 462 to initiate a second scan cycle.

If the user is satisfied with the 3D model, computing device 100 cleans up the 3D model in block 472. For example, computing device 100 can remove artifacts and finalize the stitching of the 3D model. Method 450 may subsequently proceed to block 474, where method 450 may stop.

Figure 5:
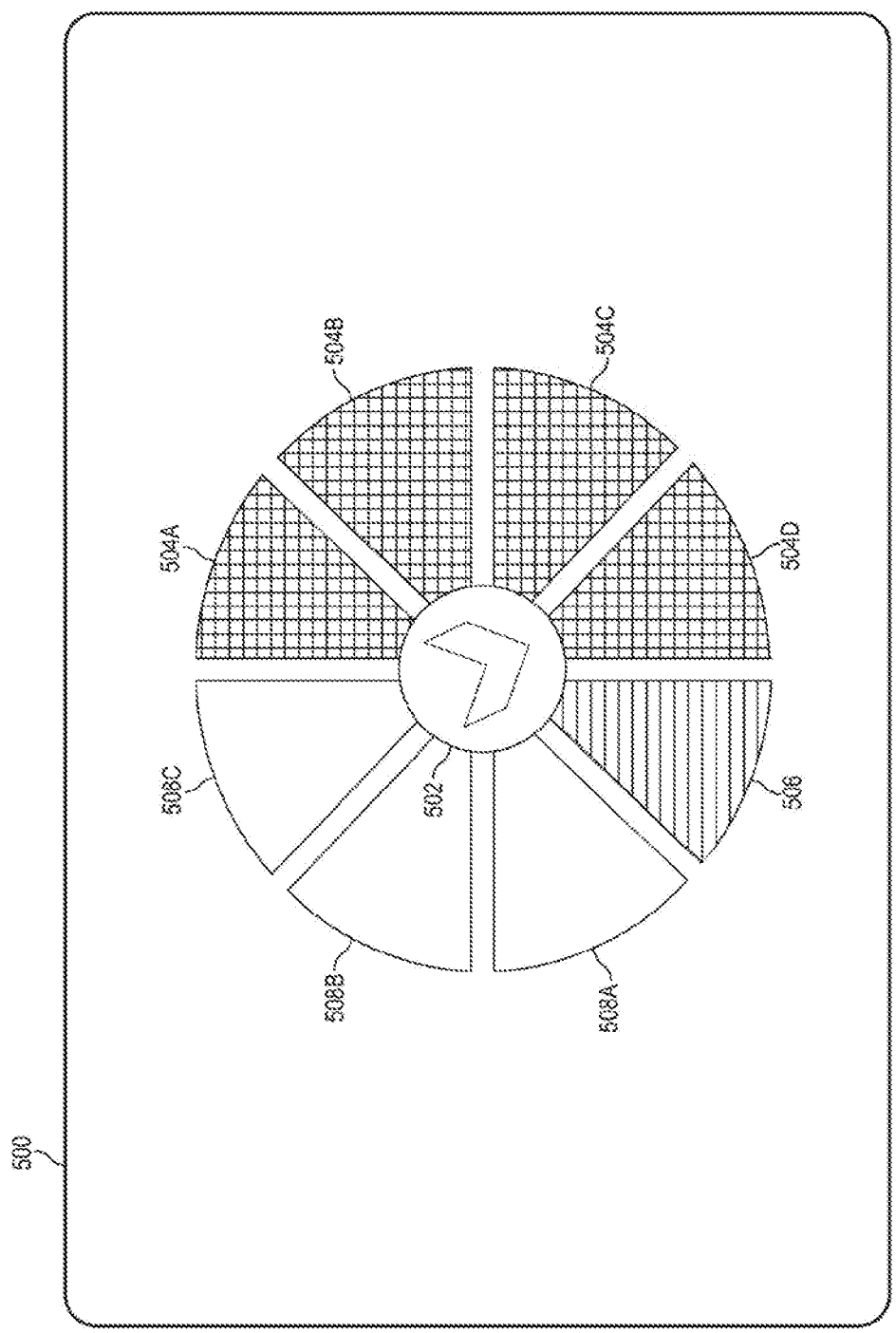
FIG. 5 is a diagram of an example user interface for providing visual cues during 3D capture technique.

FIG. 5 is a diagram of an example user interface 500 for providing visual cues during a 3D data capture. The user interface 500 can be projected onto a surface to guide a user during the 3D data capture. As depicted, user interface 500 shows a virtual rotating mechanism, which includes an object position 502, completed scan passes 504A, 504B, 504C, 504D, a next scan pass 506, and future scan passes 508A, 508B, 508C.

Object position 502 shows the position and direction of the object being scanned. As the object is moved by the user, object position 502 can be updated in real-time. When a scan pass is completed, user interface 500 is updated to show the completed pass 504A-504D. As shown, scan pass 504D has just been completed, and the user is being guided to reposition the object for the next scan pass 506. When the next scan pass 506 and future scan passes 508A-508C are completed, the scan cycle is completed. At this stage, it can be determined whether the user is satisfied with the 3D model.

The foregoing disclosure describes a number of examples for capturing and processing 3D scan data. In this manner, the examples disclosed herein enable 3D data capture by providing projected visual cues and real-time model updates that guide a user through the scanning process.

We claim:

1. A computing device for capturing and processing three dimensional (3D) scan data, the computing device comprising:
    an interface to interact with a 3D scanning device that is for scanning a real-world object to generate the 3D scan data;
    a display to present a user interface of a 3D scanning application;
    a projector to project visual cues directly on and around the real-world object; and
    a processor to:
        obtain the 3D scan data while the real-world object is repositioned in a plurality of orientations, wherein the 3D scan data comprises a plurality of 3D scan passes that are each associated with one of the plurality of orientations;
        use the projector to project visual cues that include an object position cue, a completed scan pass cue, and a next scan pass cue of the real-world object, the next scan pass cue to direct the user to reposition the real-world object to a next target position;
        following the real-world object being moved to the next target position, initiate a next scan pass of the plurality of 3D scan passes; and
        stitch the plurality of 3D scan passes to generate a 3D model of the real-world object, wherein a real-time representation of the 3D model is shown on the display as each of the plurality of 3D scan passes is incorporated into the 3D model.

2. The computing device of claim 1, further comprising a rotating mechanism to reposition the real-world object to each of the plurality of orientations while the 3D scanning device scans the real-world object.

3. The computing device of claim 2, wherein the processor is further to obtain preliminary scan data while the real-world object is continuously rotated by the rotating mechanism, wherein the 3D scanning device performs a prescan to collect the preliminary scan data; and
    generate a preliminary model of the real-world object based on the preliminary scan data, wherein the preliminary model is displayed on the user interface for review by a user.

4. The computing device of claim 1, wherein the processor is further to:
    provide cycle instructions on the display to a user to modify a tilt of the real-world object; and
    initiate a second scan cycle for the real-world object.

5. The computing device of claim 1, wherein the processor is further to use the 3D scanning device to perform a background scan of a background surface that is used to differentiate the real-world object from the background surface during the plurality of 3D scan passes.

6. A method for capturing and processing three dimensional (3D) scan data, the method comprising:
    generating a preliminary model based on a prescan of a real-world object, wherein the preliminary model is displayed on a user interface for review by a user;
    obtaining 3D scan data of the real-world object while the real-world object is repositioned in a plurality of orientations, wherein the 3D scan data comprises a plurality of 3D scan passes that are each associated with one of the plurality of orientations;
    using a projector to project visual cues that include an object position cue, a completed scan pas cue, and a next scan pass cue of the real-world object, the next scan pass cue to direct the user to reposition the real-world object to a next target position;
    following the real-world object being moved to the next target position, initiating a next scan pass of the plurality of 3D scan passes; and
    stitching the plurality of 3D scan passes to generate a 3D model of the real-world object, wherein a real-time representation of the 3D model is shown on a display as each of the plurality of 3D scan passes is incorporated into the 3D model.

7. The method of claim 6, further comprising using a rotating mechanism to reposition the real-world object to each of the plurality of orientations while a 3D scanning device scans the real-world object to obtain the 3D scan data.

8. The method of claim 6, further comprising:
    providing cycle instructions on the display to the user to modify a tilt of the real-world object; and
    initiating a second scan cycle for the real-world object.

9. The method of claim 6, further comprising using a 3D scanning device to perform a background scan of a background surface that is used to differentiate the real-world object from the background surface during the plurality of 3D scan passes.

10. A non-transitory machine-readable storage medium encoded with instructions executable by a processor for capturing and processing three dimensional (3D) scan data, wherein the instructions are to cause the processor to:

cause performance of a background scan of a background surface that is used to differentiate a real-world object from the background surface during a plurality of 3D scan passes;

generate a preliminary model based on a prescan of the real-world object, wherein the preliminary model is displayed on a user interface for review by a user;

obtain 3D scan data of the real-world object while the real-world object is repositioned in a plurality of orientations, wherein the 3D scan data comprises a plurality of 3D scan passes that are each associated with one of the plurality of orientations;

cause a projector to project visual cues that include an object position cue, a completed scan pass cue, and a next scan pass cue of the real-world object, the next scan pass cue to direct the user to reposition the real-world object to a next target position;

following the real-world object being moved to the next target position, initiate a next scan pass of the plurality of 3D scan passes; and stitch the plurality of 3D scan passes to generate a 3D model of the real-world object, wherein a real-time representation of the 3D model is shown on a display as each of the plurality of 3D scan passes is incorporated into the 3D model.

11. The machine-readable storage medium of claim 10, wherein the instructions are further to cause the processor to instruct a user to use a rotating mechanism to reposition the real-world object to each of the plurality of orientations while a 3D scanning device scans the real-world object to obtain the 3D scan data.

12. The machine-readable storage medium of claim 10, wherein the instructions are further to cause the processor to:

provide cycle instructions on the display to the user to modify a tilt of the real-world object; and cause a second scan cycle for the real-world object to be initiated.

* * * * *